United States Patent
Moriarty et al.

(10) Patent No.: US 7,182,867 B2
(45) Date of Patent: Feb. 27, 2007

(54) SHEAR-ENHANCED SYSTEMS AND METHODS FOR REMOVING WASTE MATERIALS AND LIQUID FROM THE BLOOD

(75) Inventors: Julie Moriarty, Evanston, IL (US); Rohit Vishnoi, Deerfield, IL (US); Gretchen Kunas, Pleasanton, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 11/043,370

(22) Filed: Jan. 26, 2005

(65) Prior Publication Data
US 2005/0133448 A1 Jun. 23, 2005

Related U.S. Application Data

(63) Continuation of application No. 10/066,311, filed on Feb. 2, 2002, now Pat. No. 6,863,821.

(51) Int. Cl.
*B01D 63/16* (2006.01)
*B01D 61/14* (2006.01)
*B01D 63/00* (2006.01)
*B01D 61/00* (2006.01)

(52) U.S. Cl. ............ 210/321.68; 210/321.67; 210/321.78; 210/360.1; 210/645; 210/646; 210/650

(58) Field of Classification Search ........ 210/645, 210/646, 650, 321.67, 321.68, 321.78, 360.1
See application file for complete search history.

(56) References Cited

U.S. PATENT DOCUMENTS 1,664,769 A 4/1928 Chance (Continued)

FOREIGN PATENT DOCUMENTS

DE 1 442 874 11/1963

(Continued)

OTHER PUBLICATIONS

A Thesis: Deposition Of Red Blood Cells Onto Filtering Surfaces, submitted to the faculty of the Graduate School of the University of Minnesota by Teddy William Wood, In Partial Fulfillment Of The Requirements For The Degree Of Master of Science In Mechanical Engineering, Degreed Granted Mar. 1974.

A.K. Bhagat/C.R. Wilke, "Filtration Studies with Ultrafine Particles", Sep. 1966. University of California, Lawrence Radiation Laboratory, Berkeley, CA, UCRL-16574, preprint release for announcement in Nuclear Science Abstracts.

Castino, F.: "The Filtration of Plasma From Whole Blood: A Novel Approach To Clinical Detoxification", Publication #395 from the Blood Research Laboratory, The American National Red Cross.

(Continued)

*Primary Examiner*—Krishnan S. Menon
(74) *Attorney, Agent, or Firm*—Bradford R. L. Price; Gary W. McFarron

(57) ABSTRACT

Systems and methods convey the blood through a gap defined between an inner surface that is located about an axis and an outer surface that is concentric with the inner surface. At least one of the inner and outer surfaces carries a membrane that consists essentially of either a hemofiltration membrane or a hemodialysis membrane. The systems and methods cause relative movement between the inner and outer surfaces about the axis at a selected surface velocity, taking into account the size of the gap. The relative movement of the two surfaces creates movement of the blood within the gap, which creates vortical flow conditions that induce transport of cellular blood components from the membrane while plasma water and waste material are transported to the membrane for transport across the membrane. Shear-enhanced transport of waste materials and blood plasma water results.

12 Claims, 4 Drawing Sheets

U.S. PATENT DOCUMENTS

| | | | |
|---|---|---|---|
| 2,197,509 A | 4/1940 | Reilly et al. | |
| 2,294,248 A | 8/1942 | Smulski | |
| 2,398,233 A | 4/1946 | Lincoln | |
| 2,670,849 A | 3/1954 | Dunmire | |
| 2,709,500 A | 5/1955 | Carter | |
| 3,026,871 A | 3/1962 | Thomas | |
| 3,183,908 A | 5/1965 | Collins et al. | |
| 3,355,382 A | 11/1967 | Huntington | |
| 3,396,103 A | 8/1968 | Hungtington | |
| 3,400,074 A | 9/1968 | Grenci | |
| 3,491,887 A | 1/1970 | Maestrelli | |
| 3,523,568 A | 8/1970 | van Leeuwen | |
| 3,567,030 A | 3/1971 | Loeffler et al. | |
| 3,568,835 A | 3/1971 | Hansen | |
| 3,634,228 A | 1/1972 | Latham, Jr. | |
| 3,647,632 A | 3/1972 | Johnson et al. | |
| 3,674,440 A | 7/1972 | Kitrilakis | |
| 3,705,100 A | 12/1972 | Blatt et al. | |
| 3,750,885 A | 8/1973 | Fournier | |
| 3,771,658 A | 11/1973 | Brumfield | |
| 3,771,899 A | 11/1973 | Brumfield | |
| 3,795,318 A | 3/1974 | Crane et al. | |
| 3,821,108 A | 6/1974 | Manjikian | |
| 3,830,372 A | 8/1974 | Manjikian | |
| 3,847,817 A | 11/1974 | Jarman | |
| 3,883,434 A | 5/1975 | Gayler | |
| 3,900,290 A | 8/1975 | Hornstra | |
| 3,900,398 A | 8/1975 | Gillette | |
| 3,946,731 A | 3/1976 | Lichtenstein | |
| 3,977,976 A | 8/1976 | Spaan et al. | |
| 4,040,965 A | 8/1977 | Kohlheb | |
| 4,062,771 A | 12/1977 | Saupe | |
| 4,066,554 A | 1/1978 | Guyer | |
| 4,082,668 A | 4/1978 | Zeineh et al. | |
| 4,093,552 A | 6/1978 | Guyer | |
| 4,113,614 A | 9/1978 | Rollo et al. | |
| 4,184,952 A | 1/1980 | Stewart | |
| 4,191,182 A | 3/1980 | Popovich et al. | |
| 4,212,741 A | 7/1980 | Brumfield | |
| 4,212,742 A | 7/1980 | Solomon et al. | |
| 4,214,990 A | 7/1980 | Joh | |
| 4,229,291 A * | 10/1980 | Walch et al. | 210/646 |
| 4,303,068 A | 12/1981 | Zelman | |
| 4,381,999 A | 5/1983 | Boucher et al. | |
| 4,412,553 A | 11/1983 | Kopp et al. | |
| 4,444,596 A | 4/1984 | Gortz et al. | |
| 4,486,303 A | 12/1984 | Brous | |
| 4,490,135 A | 12/1984 | Troutner | |
| 4,493,693 A | 1/1985 | Bilstad et al. | |
| 4,535,062 A | 8/1985 | Muller | |
| 4,579,662 A | 4/1986 | Jonsson | |
| 4,753,729 A | 6/1988 | Schoendorfer et al. | |
| 4,776,964 A | 10/1988 | Schoendorfer et al. | |
| 4,790,942 A * | 12/1988 | Shmidt et al. | 210/321.68 |
| 4,876,013 A | 10/1989 | Shmidt et al. | |
| 5,000,848 A * | 3/1991 | Hodgins et al. | 210/321.68 |
| 5,034,135 A | 7/1991 | Fischel | |
| 5,135,667 A | 8/1992 | Schoendorfer | |
| 5,194,145 A | 3/1993 | Schoendorfer | |
| 5,919,369 A * | 7/1999 | Ash | 210/645 |
| 6,099,730 A | 8/2000 | Ameer et al. | |
| 2003/0155312 A1 | 8/2003 | Ivansons et al. | |

FOREIGN PATENT DOCUMENTS

| | | |
|---|---|---|
| DE | 3043682 | 7/1981 |
| EP | 0 052 004 A1 | 5/1982 |
| EP | 0076665 A2 | 4/1983 |
| EP | 0112152 A2 | 6/1984 |
| FR | 1 583 221 | 10/1969 |
| GB | 1 283 273 | 9/1972 |
| GB | 1 480 406 | 7/1977 |
| SE | 771142-5 | 10/1977 |
| SU | 197801 | 11/1963 |
| WO | WO 81/02979 | 10/1981 |
| WO | WO 82/03567 | 10/1982 |
| WO | WO 82/03568 | 10/1982 |
| WO | WO 85/02783 | 7/1985 |
| WO | WO 85/04112 | 9/1985 |

OTHER PUBLICATIONS

Colton, C. K.: Fundamentals of Gas Transport in Blood, reprinted from "Artifical Lungs for Acute Respiratory Failure. Theory and Practice," W.M. Zapol and J. Qvist, Eds. Academic Press, N.Y. (1976).

Ekstein, E. C., et al.: "Self-Diffusion of Particles in Shear Flow of a Suspension", J. Fluid Mech. 1977, vol. 79, part 1, pp. 191-208.

Fordstrom, R. J., et al.: "Formed Element Deposition onto Filtering Walls", vol. XXI Trans. Amer. Soc. Artif. Int. Organs, 1975.

Gaylor, J. D., et al.,: "Gas Transfer and Thrombogenesis In An Annular Membrane Oxygenerator With Active Blood Mixing", vol. XIX Trans. Amer. Soc. Artif. Int. Organs, 1973.

Hallstrom, B., et al.: "Descriptions of a Rotating Ultra-filtration Module", Department of Food Engineering, Lund University (Sweden).

Kitrilakis, S., et al.: "A Rotating Disk Membrane Oxygenator", 1976 Hemisphere Publishing Corporation, Washington-London.

Kozinski, A. A.: "Protein Ultrafiltration: A General Example of Boundary Layer Filtration", A1ChE Journal, vol. 18, No. 5, Sep. 1972.

Lieberherr, J.: "Hydrodynamic of Annular Gap Flo Between Permeable Cylinder Walls", 532.54: 66.067.17, Escher Wyss Mitteilungen Feb. 1978-Jan. 1979.

Lopez-Leiva: "Ultrafiltration at Low Degrees of Concentration: Technical Possiblities".

Lopez-Leiva: "Ultrafiltration In Rotary Annular Flow".

Margaritis, A. and Wilke, C.: "Engineering Analysis of the Rotorfermentor", Department of Chemical Engineering and Lawrence Berkeley Laboratory, University of California 94720.

Robinson, A.: "How Does Fluid Flow Become Turbulent", Science, 221:140, Jul. 1983.

Schindhelm, K., et al.: "Mass Transfer Characteristics of Plama Filtration Membranes", Trans. Am. Soc. Artifical Organs, vol. XXVII 1981, pp. 554-558.

Schlichting, H., et al.: "Boundary-Layer Theory", 6th Ed. McGraw-Hill Series in Mechanical Engineering.

Sherwood, T.K.: Desalination by Reverse Osmosis, I & EC Fundamentals, v6 (1):2-12, Feb. 1967.

Solomon, B.A.: "Membrane Separations: Technological Principals and Issues", Trans Am Soc Artif Intern Organs 1981, pp. 345-350.

Solomon, B.A.: "Continous Flow Membrane Filtration of Plasma from Whole Blood", vol. XXIV Trans. Am. Soc. Artif. Intern. Organs, 1978.

Strong, A.B.: An Experimental Study of Mass Transfer in Rotating Coneote Flow with Low Axial Reynolds Number, The Canadian Journal of Chemical Engineering, vol. 54, Aug. 1976.

Taylor, G.I.: "Stabilityof a Viscous Liquid Cotnained Between Rotating Cylinders", Phil Trans Roy. Soc., A.223:289 (1923).

Taylor, G.I.: "Distribution of Velocity & Temperature Between Concentric Rotating Cylinders", Taylor, "Proc. Roy. Soc.," A, vol. 135, p. 698 (1932).

Tobler, W.: "Dynamic Filtraton: The Engineering Concept of the Escher Wyss Pressure Filter", Jul./Aug. 1982, Filtration & Separation.

Werynsk, A.: "Membrane Plasma Separation: Toward Improved Clinical Operation," Trans. Am. Soc. Artifical Organs, vol. XXVII 1981, pp. 554-558.

T.B. Wiltbank, et al.: "Filtration Plasmapheresis in Vivo", Transfusion, vol. 21. No. 5, pp. 502-510 (undated).

Zydney, A.L. et al.: "Continous Flow Membrane Plasmapheresis: Theoretical Models For Flux And Hemolysis Prediction".

\* cited by examiner

SHEAR-ENHANCED SYSTEMS AND METHODS FOR REMOVING WASTE MATERIALS AND LIQUID FROM THE BLOOD

RELATED APPLICATION

This application is a continuation of application Ser. No. 10/066,311, filed on Feb. 2, 2002, now U.S. Pat. No. 6,863,821 and entitled "Shear-Enhanced Systems and Methods for Removing Waste Materials and Liquids from the Blood."

FIELD OF THE INVENTION

This invention relates to systems and methods that remove waste materials and liquid from the blood of an individual whose renal function is impaired or lacking.

BACKGROUND OF THE INVENTION

For various reasons, including illness, injury or surgery, patients may require replacement or supplementation of their natural renal function in order to remove excess fluid or fluids containing dissolved waste products from their blood. Several procedures known for this purpose are hemodialysis, hemofiltration, hemodiafiltration and ultrafiltration.

SUMMARY OF THE INVENTION

The invention provides shear-enhanced systems and methods for removing waste materials and liquid from the blood.

The systems and methods convey the blood through a gap defined between an inner surface that is located about an axis and an outer surface that is concentric with the inner surface. At least one of the inner and outer surfaces carries a membrane that consists essentially of either a hemofiltration membrane or a hemodialysis membrane. The systems and methods cause relative movement between the inner and outer surfaces about the axis at a selected surface velocity, taking into account the size of the gap. The relative movement between the inner and outer surfaces creates movement of the blood within the gap, which creates a vortical flow condition that induces transport of cellular blood components from the membrane while plasma water and waste material are transported to the membrane for transport across the membrane.

The circulatory forces of the vortical flow condition clear the membrane surface of occluding cellular components to maintain efficient operation. The circulatory forces also supplement the shear forces exerted on the blood by viscous drag. Due to the circulatory forces, the concentration of waste materials in the blood plasma water becomes more homogenous. As a result, the transport of waste materials and associated blood plasma water across the membrane is significantly enhanced. Shear-enhanced waste removal makes possible the use of smaller processing devices and/or processing at reduced blood flow rates.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
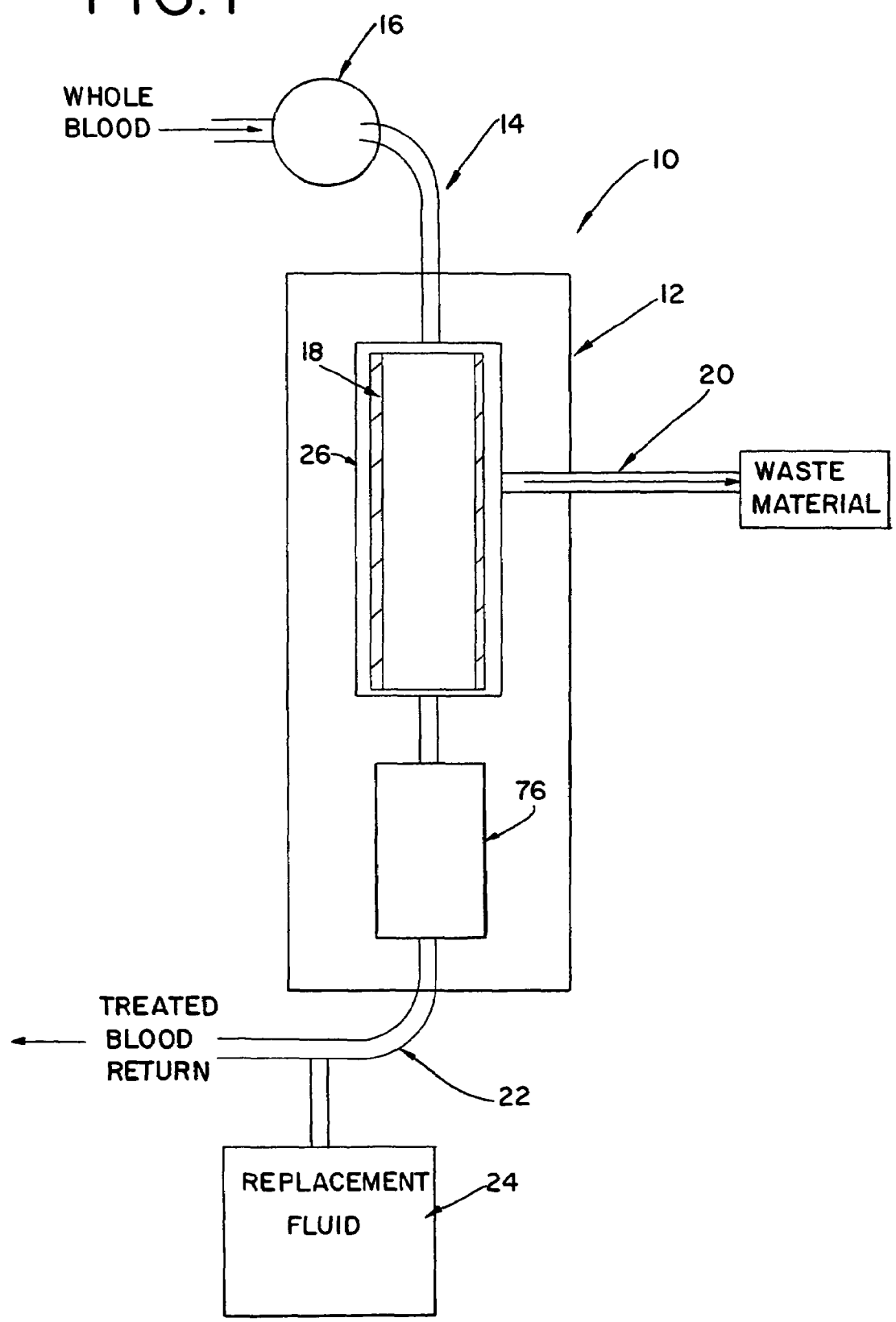
FIG. 1 is a schematic view of a system that includes a blood processing unit for removing waste material and plasma water from the blood.

FIG. 1 shows a system 10 for removing waste material (e.g., urea, creatinine, and uric acid) and plasma water from the blood of an individual whose renal function is impaired or lacking. The system 10 includes a blood processing unit 12 that receives whole blood from the individual. The individual typically has one or more surgically installed vascular access devices, such as an arterial-venous fistula, to facilitate coupling the blood processing unit 12 to the circulatory system of the individual. In the illustrated embodiment, arterial whole blood is drawn from the individual through an inlet path 14. An inlet pump 16 governs the blood inlet flow rate.

The blood processing unit 12 includes a membrane 18, along which the whole blood drawn from the individual is conveyed. The membrane 18 can have different functional and structural characteristics, which affect the manner in which waste material is transported by the membrane 18. Generally speaking, waste material carried in blood plasma water can be separated by the membrane 18 from the whole blood either by convective transport, which is driven by pressure differentials across the membrane (in a process known as hemofiltration), or by diffusion, which is driven by concentration gradients across the membrane (in a process known as hemodialysis). The waste materials and associated blood plasma water are removal from the blood processing unit 12 through a waste path 20 for discard.

The pores of the membrane 18 desirably have a molecular weight cut-off that block the passage of cellular blood components and larger peptides and proteins (including albumin) across the membrane. These components are retained in the blood, which is conveyed from the blood processing unit 12 through an outlet path 22 for return to the individual. In the illustrated embodiment, the treated blood is returned to the venous blood circulatory system of the individual.

Fresh physiologic fluid, called replacement fluid, is typically supplied from a source 24 to the plasma water and toxin-depleted blood. The replacement fluid restores, at least partially, a normal physiologic fluid and electrolytic balance to the blood returned to the individual.

The relative volumes of waste plasma water removed and replacement fluid supplied can be monitored, e.g., by gravimetric means, so that a desired volumetric balance can be achieved. An ultrafiltration function can also be performed by the blood processing unit 12, by which plasma water is replaced in an amount slightly less than that removed. Ultrafiltration decreases the overall fluid level of the individual undergoing treatment, which typically increases due to normal fluid intake between treatment sessions.

The blood processing unit 12 includes a processing cartridge 26, in which the membrane 18 is housed. The cartridge 26 is desirable disposable and, in one representative embodiment (see FIG. 2), includes a generally cylindrical housing 28, which is sized to be conveniently manipulated by an operator. The housing 28 can be oriented for use either horizontally or vertically, or any intermediate position.

An elongated cylindrical rotor 30 (which can also be called a "spinner") is rotatably supported within the housing 28 between oppositely spaced pivot bearings 32 and 34. The rotor 30 rotates within the housing 28, which is held stationary during use. However, other manners of operation are possible, and the housing need not be held stationary.

An annular gap 36 is formed between the outer surface of the rotor 30 and the interior wall 38 of the housing 28. Whole blood in the inlet path 14 is conveyed through a blood inlet port 40 into the gap 36 for processing by the inlet pump 16. After processing, the blood is discharged from the gap 36 through an oppositely spaced outlet port 42, which communicates with the blood return path 22.

In the illustrated embodiment, a magnetic drive assembly 44 provides rotation to the rotor 30. A ring of magnetic material 46 in the rotor 30 is acted upon by a rotating magnetic field generated by an external, rotating magnetic drive member 48, which releasably engages the adjacent end of the housing 28 for use. The rotor 30 rotates relative to the stationary interior wall 38 of the housing 28. The magnetic drive member 48 rotates the rotor 30 at a predetermined angular velocity.

Further details regarding devices employing a spinning rotor and a stationary housing for blood filtration can be found in U.S. Pat. No. 5,194,145 and U.S. Pat. No. 4,965,846, which are incorporated herein by reference.

Figure 2:
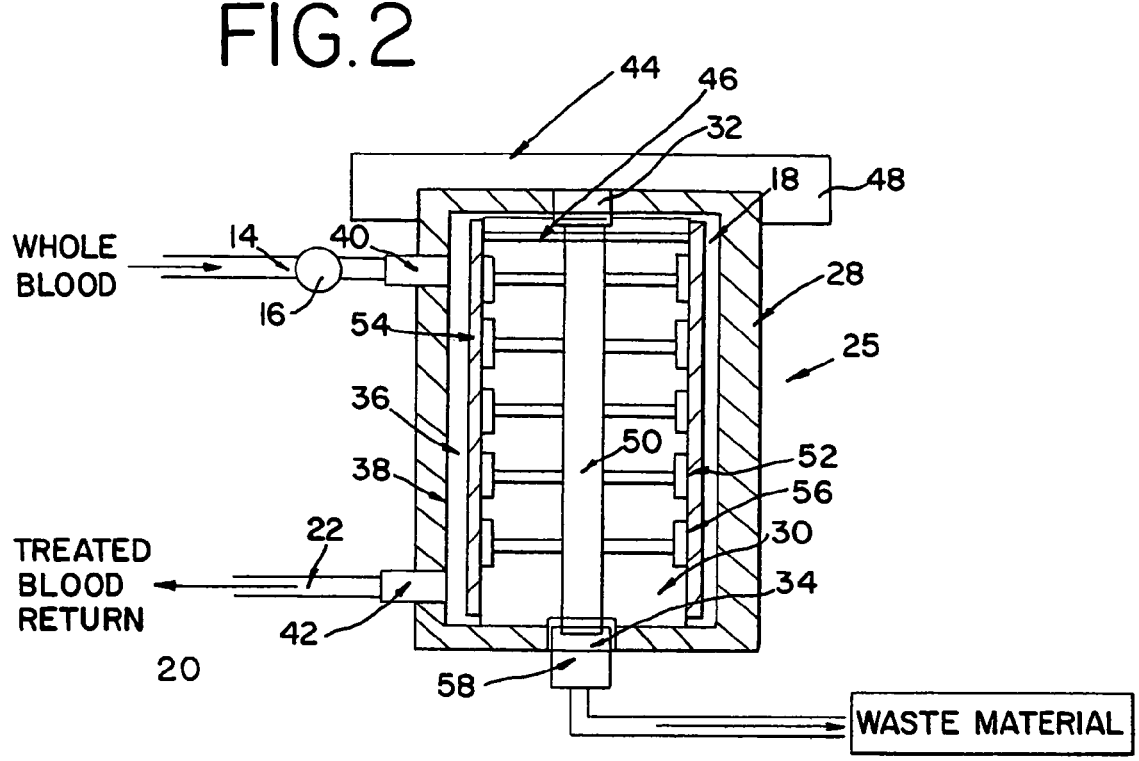
FIG. 2 is a side section view of one embodiment of a blood processing unit that the system shown in FIG. 1 can incorporate for the purpose of performing shear-enhanced hemofiltration.
Figure 3:
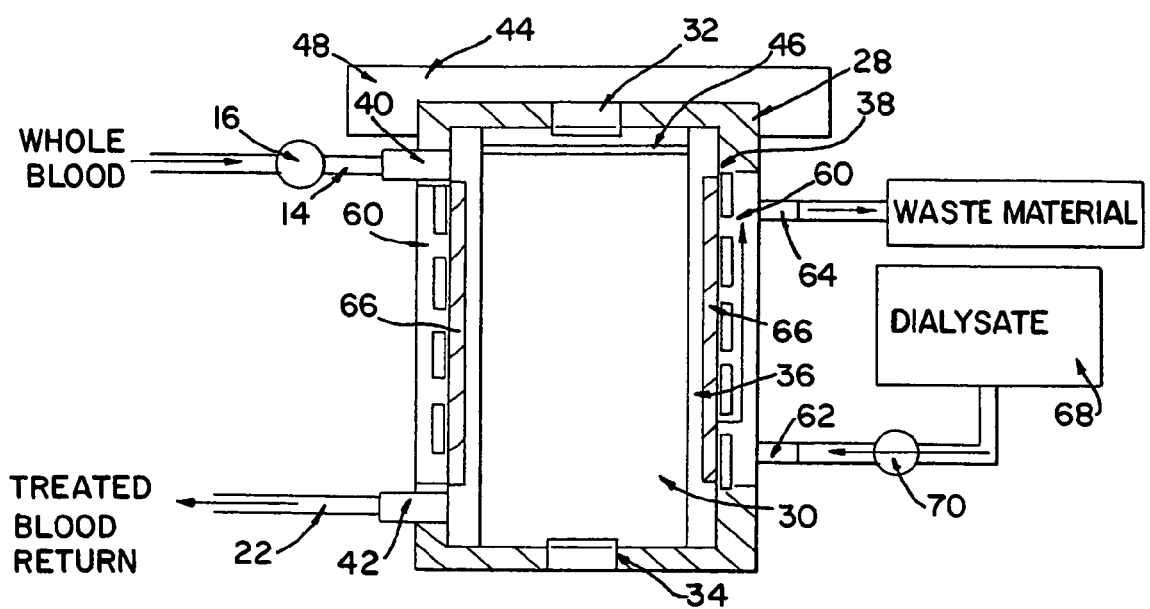
FIG. 3 is a side section view of another embodiment of a blood processing unit that the system shown in FIG. 1 can incorporate for the purpose of performing shear-enhanced hemodialysis.
Figure 4:
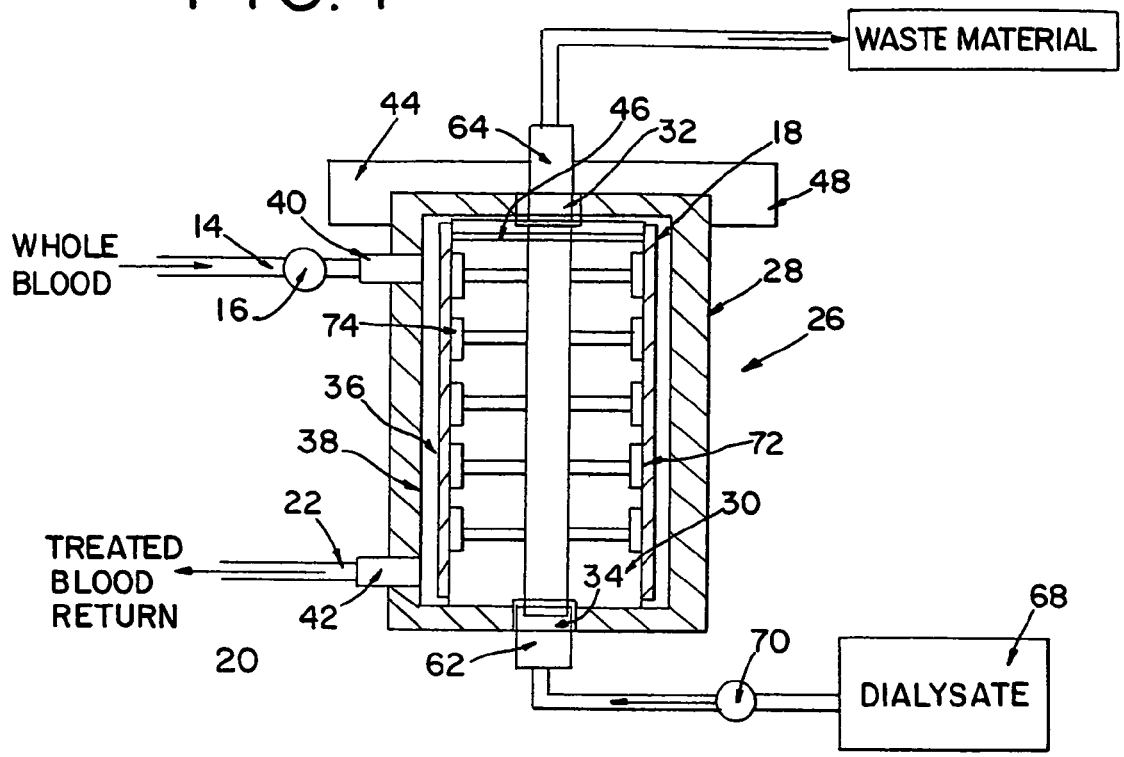
FIG. 4 is a side section view of another embodiment of a blood processing unit that the system shown in FIG. 1 can incorporate for the purpose of performing shear-enhanced hemodialysis.
Figure 5:
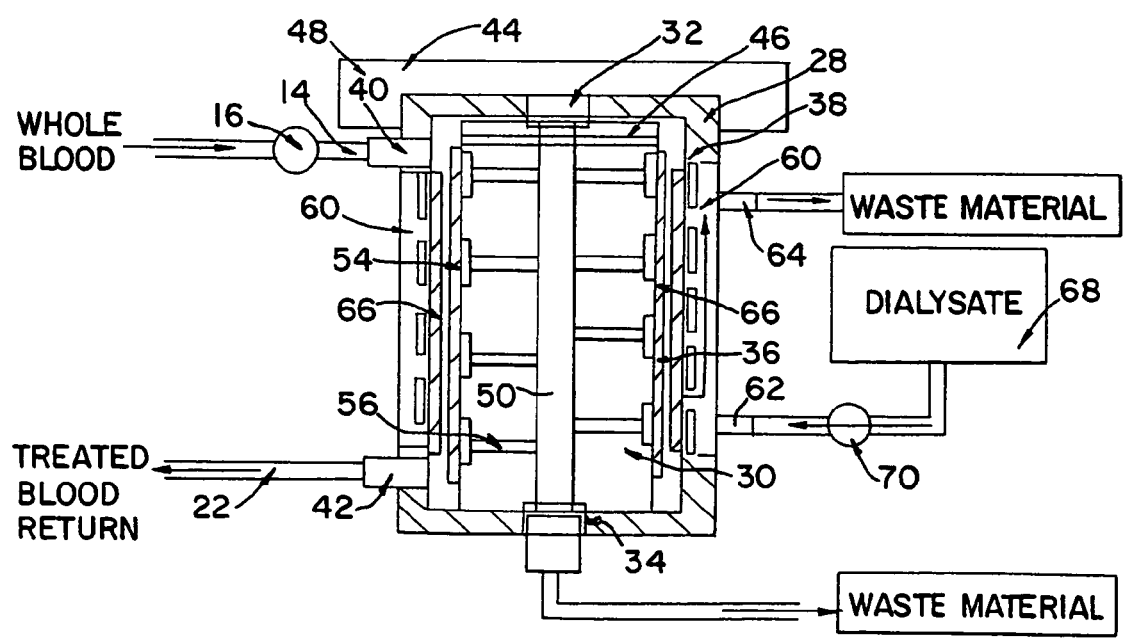
FIG. 5 is a side section view of another embodiment of a blood processing unit that the system shown in FIG. 1 can incorporate for the purpose of performing shear-enhanced hemofiltration and hemodialysis.

Further details of construction and operation of the processing cartridge 26 can differ, depending upon the type of blood processing sought to be performed. If hemofiltration is to be performed, the membrane 18 comprises an appropriate hemofiltration membrane (as FIG. 2 shows). If hemodialysis is to be performed, the membrane 18 comprises an appropriate hemodialysis membrane (as FIGS. 3 and 4 show). If hemodialysis with hemofiltration is to be performed, the processing cartridge 26 can include both a hemofiltration membrane and a hemodialysis membrane (as FIG. 5 shows).

A. Hemofiltration

In the embodiment shown in FIG. 2, the rotor 30 has an internal cavity 50 bounded by a grooved cylindrical wall 52 forming a network of channels 56. A hemofiltration membrane 54 covers the outer surface of grooved wall 52. The hemofiltration membrane 54 can comprise, e.g., a biocompatible synthetic material such as polysulfone, polyacrylonitrile, polymethylmethacrylate, polyvinyl-alcohol, polyamide, polycarbonate, etc., and cellulose derivatives. The pores of hemofiltration membrane 54 desirably allow passage of molecules up to about 30,000 Daltons, and desirably not greater than about 50,000 Daltons, to avoid the passage of albumin (molecular weight of 68,000 Daltons).

The network of channels 56 convey blood plasma water passing through the membrane 54 into the cavity 50. An outlet port 58 communicates with the cavity 50 to convey blood plasma water from the processing cartridge 26.

In operation, as the rotor 30 is rotated, the pump 16 conveys whole blood into the gap 36. The whole blood flows within the gap 36 in contact with the hemofiltration membrane 54.

In response to the transmembrane pressure created by the pump 16, waste material and associated blood plasma water flow from the gap 36 through membrane 54 into the channels 56. Waste material and associated blood plasma water are discharged from the processing cartridge through the outlet port 58. Cellular blood components continue to flow within the gap 36 for discharge through the outlet port 42.

It should be appreciated that, alternatively, the hemofiltration membrane 54 can be mounted on the stationary wall 38 of the housing 28, instead of being mounted on the spinning rotor 30, as FIG. 2 shows. In this arrangement, the network of channels 56 communicating with the waste outlet port 58 would be formed in the stationary wall 38, and the membrane 54 would overlay the channels in the same fashion shown in FIG. 2. It should also be appreciated that, alternatively, a hemofiltration membrane 54 can be mounted on both the spinning rotor 30 and the stationary wall 28 and used in tandem for waste material and plasma water removal.

B. Hemodialysis

In the embodiment shown in FIG. 3, the interior wall 38 of the housing 28 has a network of channels 60 communicating with an inlet port 62 and an outlet port 64. A semipermeable hemodialysis membrane 66 overlays the network of channels 60. The membrane 66 can, e.g., comprise a medium to high flux membrane, for example, a polysulfone, cellulose triacetate or acrylonitrile membrane. Such membranes are typically well suited to fluid and small solute (less the 10,000 Daltons) removal. One side of the membrane 66 faces the annular gap 36 and the rotor 30, which, in the illustrated embodiment, carries no membrane. The other side of the membrane 66 faces the channels 60.

In operation, as the rotor 30 is rotated, the pump 16 conveys whole blood into the gap 36. The whole blood flows within the gap 36 in contact with membrane 66. Fresh dialysate is circulated by a pump 70 from a source 68 through the channels 60 via the ports 62 and 64. Desirably (as FIG. 3 shows), the dialysate is circulated through the channels 60 in a flow direction opposite to the direction of whole blood flow in the gap 36.

As blood flows through the gap 36, plasma water is conveyed across the membrane 66 due to transmembrane pressure created by the pump 16. Targeted waste materials are also transferred across the membrane 66 by diffusion, due to a difference in concentration of these materials in the blood (high concentrations) and in the fresh dialysate (low concentrations). In response to the high-to-low concentration gradient, waste materials flow from the gap 36 through the membrane 66 into the dialysate. The waste materials are discharged with the spent dialysate out of the processing cartridge 26 to, e.g., a drain. Cellular blood components continue to-flow within the gap 36 for discharge through the outlet port 42 for return to the individual.

As shown in FIG. 4, in an alternative embodiment, the rotor 30 can include a network of channels 72 through which dialysate can be circulated in the manner just described. In this arrangement, a hemodialysis membrane 74 overlays the network of channels 72 on the rotor 30. One side of the membrane 74 faces the annular gap 36. The other side of the membrane faces the channels 72.

It should be appreciated that the hemodialysis membrane 74 on the rotating rotor 36 can also be used in combination with the hemodialysis membrane 66 on the stationary interior wall 38 of the housing 28, or by itself (in which case the stationary interior wall 38 of the housing 28 would be free of a membrane.

As shown in FIG. 5, the processing cartridge 26 can include a hemodialysis membrane 66 mounted on either the rotor 30 or the interior housing wall 38 and a hemofiltration membrane 54 mounted on the other location. In this arrangement, the processing cartridge 26 accommodates hemdialysis with hemofiltration, a process also called hemodiafiltration.

C. Shear-Enhanced Waste Removal

Figure 6:
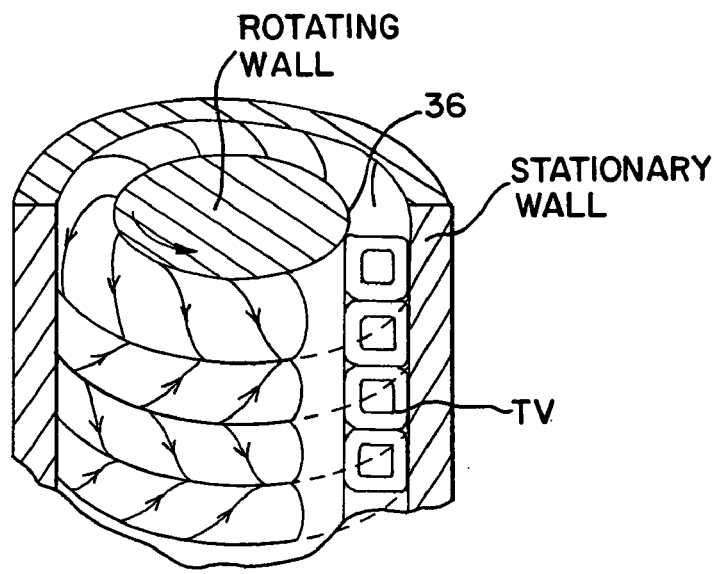
FIG. 6 is an enlarged and simplified perspective view of a gap formed between a stationary and rotating concentric surfaces, of a type that the blood processing units shown in FIGS. 2 to 5 incorporate, in which vortical flow conditions provide shear-enhanced waste material and plasma water removal.

In an annular gap 36 as just described, which is defined between two concentric surfaces (e.g., the rotor 30 and the interior housing wall 38), rotation of the inner surface relative to the outer surface can induce vortical flow conditions in the blood residing in the gap 36. The vortical flow conditions take the form of successive, alternately circulating, annuli TV (see FIG. 6) in the gap 36 between the two concentric surfaces. This vortex action can be a type that can be generally classified as "Taylor vortices" (as designated as TV in FIG. 6). The nature of the Taylor vortices can vary among laminar stable Taylor vortices, wavy non-stable Taylor vortices, turbulent Taylor vortices, or other intermediate vortical flow conditions.

Taylor vortices will develop in the blood occupying the gap 36, regardless of whether the membrane is mounted on the inner surface or on the outer surface, or both surfaces. Taylor vortices develop in the blood occupying the gap 36 as a result of relative movement between the inner and outer surfaces, regardless of whether one of the surfaces is held stationary while the other rotates, or whether both surfaces are allowed to rotate. To achieve desired vortical flow conditions, it is believed that the inner surface should be rotated relative to the outer surface, and, if the outer surface is allowed to rotate, the rate of rotation of the inner surface should exceed the rate of rotation of the outer surface.

The amplitude of the vortex action, which is characterized by the Taylor number, is a function of the rate of rotation of the rotating surface and the radial dimension of the gap 36. At a given radial dimension, increasing the rate of rotation will increase the amplitude of the vortex action, leading to a higher Taylor number. Given a rate of rotation, narrowing the radial dimension of the gap 36 will also increase the amplitude vortex action, leading to a higher Taylor number. It is believed that radial dimension of the gap 36 and the rate of rotation should be selected to yield a Taylor number that is greater than the critical Taylor number, at which vortical flow conditions develop.

Transmembrane pressure is also desirably monitored and maintained (by controlling operation of the pump 16) at a magnitude that maximizes fluid transport across the membrane without driving cellular blood components into the membrane pores, which can cause membrane plugging, hemolysis, and trauma to fragile cellular blood components residing within the gap 36.

Figure 7:
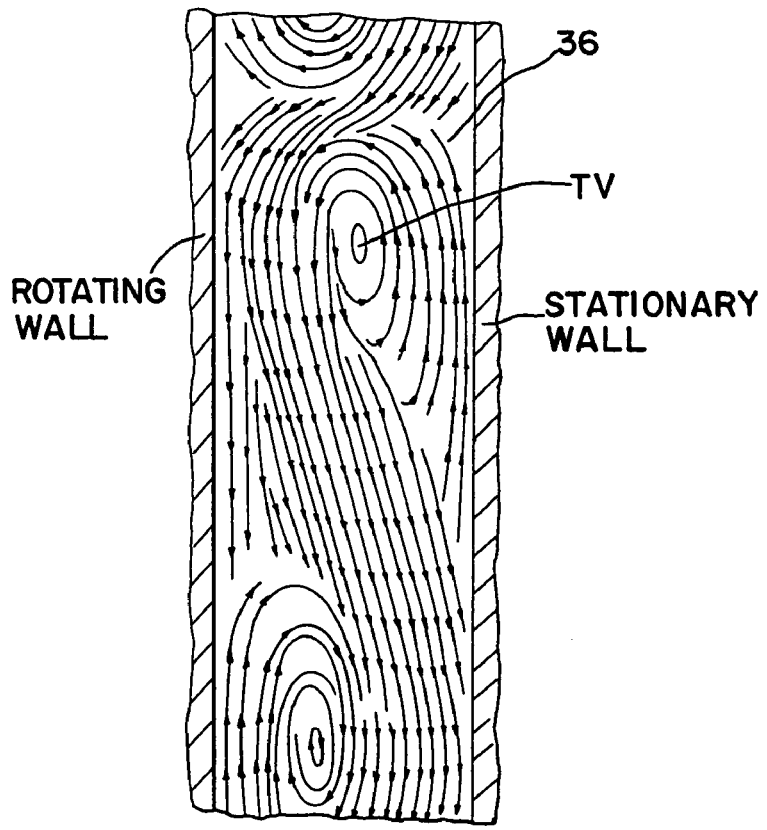
FIG. 7 is an enlarged side sectional view of the vortical flow conditions shown in FIG. 5 that provide shear-enhanced waste material and plasma water removal.

When maintained within desired limits, the vortical flow conditions provide a sweeping action in the gap 36 (see FIG. 7) that transports cellular blood components away from the membrane while blood plasma water carrying the targeted uremic toxins is transported to the membrane for passage through the pores of the operative membrane. The circulation caused by the vortical flow conditions removes adherent cellular blood components from the surface of the operative membrane and replenishes available blood plasma water for transport through the membrane pores. The vortical flow conditions thereby clear the membrane surface of occluding cellular components to maintain efficient operation at desirable transmembrane pressure levels. The circulatory forces also supplement the shear forces exerted on the blood by viscous drag, which is tangential to the spinning membrane surface. Furthermore, due to the circulatory forces, the concentration of waste materials in the blood plasma water becomes more homogenous. In all, the transport of waste materials and associated blood plasma water across the membrane is significantly enhanced. Shear-enhanced waste removal makes possible the use of smaller processing devices and/or processing at reduced blood flow rates.

If desired, ultrafiltration volume can be augmented by placing, either upstream or downstream of the processing cartridge 26, an auxiliary processing cartridge 76 (shown in phantom lines in FIG. 1). The auxiliary processing cartridge 76 subjects the blood to plasma water removal (either by hemodialysis or hemofiltration) in addition to the plasma water removal by the processing cartridge 26. An auxiliary processing cartridge 76 can also be used in series with the processing cartridge 26, to provide waste removal by hemofiltration to augment waste removal by hemodialysis conducted by the processing cartridge 26, or vice versa.

Various features of the invention are set forth in the following claims.

We claim:

1. A system for removing waste from the blood of an individual comprising an access device for withdrawing blood from an individual;

a blood processing device, including an inlet;

a first flow path in fluid communication between said access device and said inlet for conveying whole blood from the individual to said blood processing device;

said blood processing device comprising a gap defined between an inner surface that is located about an axis and an outer surface that is concentric with the inner surface, said inlet and a first outlet communicating with the gap for continuous flow of blood between the inlet and the first outlet, at least one of the inner and outer surfaces carrying a hemofiltration membrane having one surface facing the gap and another surface facing away from the gap and said membrane having a pore size sufficiently small to prevent passage of molecules greater than about 50,000 Daltons so as to prevent the passage of albumin, a driver causing relative movement between the inner and outer surfaces about the axis at a selected surface velocity, taking into account the size of the gap, to create movement of the blood within the gap that induces transport of cellular blood components from the membrane while plasma water and waste material are transported to the membrane for transport across the membrane;

a second flow path in fluid communication with the first outlet for conveying blood components from said processing device for return to the individual;

a second outlet communicating with the membrane surface facing away from the gap; and a third flow path in communication with said second outlet for conveying plasma water and waste material away from said blood processing device.

2. A system according to claim 1
wherein the hemofiltration membrane includes a first surface facing toward the gap and a second surface facing away from the gap, and
wherein the blood processing device includes a channel along the second surface of the hemofiltration membrane to convey waste material transported across the hemofiltration membrane.

3. A system according to claim 1
wherein the drive mechanism rotates the inner surface while holding the outer surface stationary.

4. A system according to claim 1
wherein the drive mechanism rotates the inner surface at a higher rate of rotation than the outer surface.

5. A system according to claim 1
wherein the other of the inner and outer surfaces carry a membrane that consists essentially of at least one of a hemofiltration membrane and a hemodialysis membrane.

6. A system according to claim 5
wherein both surfaces carry a hemofiltration membrane.

7. A method for removing waste from the blood of an individual comprising the steps of
continuously conveying blood from an individual through a first flow path communicating between such individual and an inlet into a gap defined between an inner surface that is located about an axis and an outer surface that is concentric with the inner surface, at least one of the inner and outer surfaces carrying a hemofiltration membrane having one surface facing the gap and another surface facing away from the gap and having a pore size sufficiently small to prevent passage of molecules greater than about 50,000 Daltons so as to prevent the passage of albumin,
causing relative movement between the inner and outer surfaces about the axis at a selected surface velocity, taking into account the size of the gap, to create movement of the blood within the gap that induces transport of cellular blood components from the membrane through the gap while plasma water and waste material are transported to the membrane for transport across the membrane;
returning blood components to the individual through a second flow path in fluid communication between the gap and said individual, and
conveying the plasma water and waste material through a third flow path in fluid communication with the surface of the membrane facing away from the gap.

8. A method according to claim 7
further including the step of conveying away material that is transported across the hemofiltration membrane.

9. A method according to claim 7
wherein the inner surface is rotated while holding the outer surface stationary.

10. A method according to claim 7
wherein the inner surface is rotated at a higher rate of rotation than the outer surface.

11. A method according to claim 7
wherein the other of the inner and outer surfaces carry a membrane that consists
essentially of at least one of a hemofiltration membrane or a hemodialysis membrane.

12. A method according to claim 11
wherein both surfaces carry a hemofiltration membrane.

* * * * *